United States Patent [19]

Inamasa et al.

[11] Patent Number: 5,276,230
[45] Date of Patent: Jan. 4, 1994

[54] PROCESS FOR PRODUCTION OF 2,6-DIMETHYLNAPHTHALENE

[75] Inventors: Kenji Inamasa; Norio Fushimi; Makoto Takagawa, all of Tsukuba, Japan

[73] Assignee: Mitsubishi Gas Chemical Company, Inc., Tokyo, Japan

[21] Appl. No.: 944,363

[22] Filed: Sep. 14, 1992

[30] Foreign Application Priority Data

Dec. 6, 1991 [JP] Japan .................. 3-323072

[51] Int. Cl.$^5$ .................. C07C 5/00
[52] U.S. Cl. .................. 585/320; 585/26; 585/410; 585/411
[58] Field of Search ........... 583/407, 320, 411, 410; 585/26

[56] References Cited

U.S. PATENT DOCUMENTS

| | | | |
|---|---|---|---|
| 3,931,348 | 1/1976 | Taniguchi et al. | 585/418 |
| 5,008,479 | 4/1991 | Abe et al. | 585/320 |
| 5,023,390 | 6/1991 | Abe et al. | 585/411 |
| 5,068,480 | 11/1991 | Takagawa et al. | 502/60 |

FOREIGN PATENT DOCUMENTS

| | | |
|---|---|---|
| 60-45536 | 3/1985 | Japan . |
| 60-172937 | 9/1985 | Japan . |
| 62-29536 | 2/1987 | Japan . |
| 63-8344 | 1/1988 | Japan . |
| 63-14737 | 1/1988 | Japan . |
| 3-173834 | 7/1991 | Japan . |
| 3-251545 | 11/1991 | Japan . |

OTHER PUBLICATIONS

Chemical Abstracts, vol. 83, No. 19, Nov. 10, 1975, Columbus, Ohio, US; Abstract No. 163903z, p. 523; & JP-A-75 012 429 (Teijin).

*Primary Examiner*—Anthony McFarlane
*Attorney, Agent, or Firm*—Frishauf, Holtz, Goodman & Woodward

[57] ABSTRACT

There is disclosed a process for efficiently producing 2,6-dimethylnaphthalene used for the production of polyethylene naphthalate which comprises subjecting 2-methyl-1-(p-tolyl)butene and/or 2-methyl-1-(p-tolyl)butane as a starting raw material to cyclization dehydrogenation reaction by the use of a catalyst comprising a platinum component and at least one component selected from the group consisting of alkali metals and alkaline earth metals each being supported on aluminum oxide. The above process enables the production of the objective compound in a high yield at a low cost by using the catalyst having high safety and stability from the widely available starting material, thereby enhancing the industrial significance of the process.

12 Claims, No Drawings

PROCESS FOR PRODUCTION OF 2,6-DIMETHYLNAPHTHALENE

BACKGROUND OF THE INVENTION

1. Field of the Invention

The present invention relates to a process for production of 2,6-dimethylnaphthalene. More particularly, it pertains to a process for efficiently producing 2,6-dimethylnaphthalene useful as a starting raw material for 2,6-naphthalene dicarboxylic acid by the use of a specific catalyst.

2. Description of Related Art

Polyethylene naphthalate which is obtained by the condensation reaction of 2,6-naphthalene dicarboxylic acid with ethylene glycol is excellent in tensile strength and heat resistance and is widely used for fibers and films.

2,6-Naphthalene dicarboxylic acid which is subjected to condensation reaction in the production of polyethylene naphthalate is generally derived from 2,6-dimethylnaphthalene, which has an industrially important use as a starting raw material for the production of such high-performance polyester.

2,6-Dimethylnaphthalene has heretofore been obtained by isolating it from a coal tar fraction or a fraction of heavy oil subjected to fluid catalytic cracking (FCC). However, the aforementioned isolation process affords the fraction in the form of mixture containing almost all the types of methyl group-position isomers such as 1,2-, 1,3-, 1,4-, 1,5-, 1,6-, 1,7-, 1,8-, 2,3- and 2,7-dimethylnaphthalene in addition to the objective 2,6-dimethylnaphthalene. Thus, the process for isolating and purifying 2,6-dimethylnaphthalene from such fraction mixture suffers the disadvantage of a number of steps and high cost required in the production thereof, making itself unsuitable for inexpensive mass-production of 2,6-dimethylnaphthalene.

There have recently been proposed several processes for producing 2,6-dimethylnaphthalene from a variety of starting raw materials, but there has not yet been established an industrial production process capable of efficiently and selectively synthesizing 2,6-dimethylnaphthalene by the use of inexpensive starting raw material available in a large quantity.

Examples of the above-mentioned process include the process disclosed in Japanese Patent Application Laid-Open Nos. 172937/1985, 29536/1987 and 8344/1988 in which naphthalene or monomethylnaphthalene is methylated into dimethylnaphthalene and the process disclosed in Japanese Patent Application Laid-Open Nos. 45536/1985 and 14737/1988 in which naphthalene or monomethylnaphthalene is transmethylated into dimethylnaphthalene by using polymethylbenzene.

Nevertheless, the process disclosed in any of the aforesaid Laid-Open Patent Applications suffers from the defects that the conversion of naphthalene and monomethylnaphthalene is low and selective production of 2,6-dimethylnaphthalene is difficult. Consequently, the process necessitates complicated isolating purification steps and intricate isomerization steps, thus causing disadvantageous problem from the industrial point of view.

In addition, Japanese Patent Application Laid-Open Nos. 61647/1973 and 48647/1974 disclose the process for production of 2,6-dimethylnaphthalene by cyclization, dehydrogenation and isomerization of 5-(o-tolyl)-pentene-2 to be used as a starting material. Moreover, Japanese Patent Publication Nos. 17983/1975, 17985/1975 and 22550/1975 disclose the process for producing dimethylnaphthalene by cyclization dehydrogenation of 5-(o-tolyl)pentene-2.

In the above-mentioned processes, however, 5-(o-tolyl)pentene-2 to be used as a starting material is usually produced from o-xylene and 1,3-butadiene by the use of an alkali metal such as potassium or sodium as a catalyst, and many problems remain unsolved with regard to the catalyst handling especially in safety. Likewise, as the resultant dimethylnaphthalene is obtained as the mixture of isomers such as 1,5-dimethylnaphthalene, 1,6-dimethylnaphthalene, 2,6-dimethylnaphthalene and the like, the production of 2,6-dimethylnaphthalene therefrom suffers a lot of disadvantages that the steps of isomerization, separation and purification are necessary.

On the other hand, there has been developed a process for selectively producing 2,6-dimethylnaphthalene by cyclization and dehydrogenation of 2-methyl-1-(p-tolyl)butene or 2-methyl-1-(p-tolyl)butane as disclosed, for example, in Japanese Patent Publication No. 5292/1978 wherein a catalyst comprising rhenium oxide, an alkali metal oxide or alkaline earth metal oxide and alumina is used, and in Japanese Patent Publication No. 1701/1976 wherein a catalyst of chromia/alumina series containing an alkali metal oxide is employed.

However, the above-disclosed catalysts are unfavorable, since the use thereof results in a low yield and an insufficient purity of the objective 2,6-dimethylnaphthalene; besides the highly toxic chrominum compound therein will bring about environmental pollution problem.

It has been discovered by the present inventors, as disclosed in Japanese Patent Application Laid-Open Nos. 173834/1991 and 251545/1991, that in the production of 2,6-dimethylnaphthalene by cyclization dehydrogenation of 2-methyl-1-(p-tolyl)butene or 2-methyl-1-(p-tolyl)butane, 2,6-dimethylnaphthalene with high purity is obtained at a relatively high yield by the application of the catalyst comprising lead and alumina, or indium and alumina, as essential components.

Nevertheless, the above-developed catalysts still involve some problems such that the catalyst containing a lead component is industrially unfavorable due to its toxicity and the catalyst containing an indium component sometimes evaporates away during its use owing to the high volatility of a monovalent indium compound formed during the reaction and the like. Under such circumstances, it has been sought for a long time to develop a catalyst capable of producing highly pure 2,6-dimethylnaphthalene at a high yield with stabilized operation without causing any problem relating to sanitation.

In view of the above, intensive research and investigation were concentrated by the present inventors on the process for cyclization dehydrogenation of 2-methyl-1-(p-tolyl) butene, 2-methyl-1-(p-tolyl)butane and mixture thereof. As a result, it has been discovered by the present inventors that highly pure 2,6-dimethylnaphthalene is obtained at a high yield by the use of a catalyst comprising a platinum component and at least one compound selected from alkali metal compounds and alkaline earth metal compounds each being supported on aluminum oxide. The present invention has been accomplished on the basis of the above-mentioned finding and information.

SUMMARY OF THE INVENTION

It is the general object of the present invention to provide a process for efficiently producing 2,6-dimethylnaphthalene.

It is another object of the present invention to provide a process for producing highly pure 2,6-dimethylnaphthalene at a high yield by the use of an inexpensive starting raw material available in a large quantity.

It is still another object of the present invention to provide a catalyst for use in the process for efficiently producing 2,6-dimethylnaphthalene by cyclization dehydrogenation of a starting raw material.

Other objects of the present invention will be obvious from the description of this text hereinafter disclosed.

Specifically, the present invention provides a process for production of 2,6-dimethylnaphthalene which comprises subjecting 2-methyl-1-(p-tolyl)butene, 2-methyl-1-(p-tolyl)butane or mixture thereof as a starting raw material to cyclization dehydrogenation reaction by the use of a catalyst comprising a platinum component and at least one component selected from the group consisting of alkali metals and alkaline earth metals each being supported on aluminum oxide as well as the aforestated catalyst.

DESCRIPTION OF PREFERRED EMBODIMENT

In the case where 2-methyl-1-(p-tolyl)butene or 2-methyl-1-(p-tolyl)butane as a starting material is reacted by the use of a catalyst consisting of aluminum oxide alone, dimethylnaphthalene is generally produced but the yield thereof is too low and unfavorable side reaction such as isomerization, decomposition and polymerization of the starting material is too excessive to make the catalyst industrially usable.

The application of a catalyst consisting of aluminum oxide incorporated with a platinum component to the above reaction improves the selectivity to cyclization dehydrogenation and increases the yield of dimethylnaphthalene, but remarkable side reaction such as isomerization and demethylation of the resultant dimethylnaphthalene takes place together with decomposition and polymerization of the starting material, unfavorably lowering the selectivity to the objective 2,6-dimethylnaphthalene.

On the other hand, the application of a catalyst consisting of an alkali metal component or alkaline earth metal component each supported on aluminum oxide can suppress decomposition and polymerization of 2-methyl-1-(p-tolyl)butene or 2-methyl-1-(p-tolyl)butane as the starting material, but the catalyst scarcely exhibits cyclization dehydrogenation activity or even if it exhibits the activity, the yield of dimethylnaphthalene is too low to make the catalyst industrially usable.

Specifically, the use of a catalyst consisting only of aluminum oxide causes a lot of side reactions due to acid points on the surface of the catalyst including isomerization, decomposition and polymerization of the starting material to take place in the reaction process. By moderating the too strong acid points on the above-mentioned catalyst with an alkali metal compound or alkaline earth metal compound and at the same time, incorporating a platinum component having intense dehydrogenation ability in the catalyst, the catalyst according to the present invention can drastically improve the reaction selectivity directed to 2,6-dimethylnaphthalene in cyclization dehydrogenation reaction of 2-methyl-1-(p-tolyl)butene or 2-methyl-1-(p-tolyl)butane.

Such being the case, by the use of the catalyst according to the present invention, isomerization to other isomers than the objective 2,6-dimethylnaphthalene is suppressed, reaction selectivity directed to and yield of the objective 2,6-dimethylnaphthalene is drastically improved and industrially safe operation is assured without the formation of toxic substance or volatile matter during the reaction.

In the catalyst according to the present invention, the amount of the platinum component supported on aluminum oxide is 0.05 to 20%, preferably 0.1 to 10% by weight expressed in terms of metallic platinum based on the amount of aluminum oxide. An amount of the platinum component less than 0.05% by weight results in insufficient dehydrogenation capacity and low conversion efficiency of the starting material such as 2-methyl-1-(p-tolyl)butene or 2-methyl-1-(p-tolyl)butane, whereas that exceeding 20% by weight brings about an expensive catalyst due to a large usage of metallic platinum, making the catalyst impractical.

In addition, in the catalyst according to the present invention, the amount of the alkali metal compound or alkaline earth metal compound is 0.1 to 20%, preferably 1 to 10% by weight expressed in terms of alkali or alkaline earth metal based on the amount of aluminum oxide. An amount of the alkali or alkaline earth metal less than 1% by weight leads to insufficient adjustment of acid points for alumina causing remarkable isomerization, decomposition, polymerization or the like of 2-methyl-1-(p-tolyl)butene or 2-methyl-1-(p-tolyl)butane as the starting material, while that exceeding 10% by weight is unfavorable, since it fails to embody the catalytic activity and suppresses cyclization dehydrogenation reaction.

Examples of alkali metals include the metals belonging to the group I of Periodic Table such as sodium, potassium, lithium and cesium. Examples of alkaline earth metals include the metals belonging to the group II of Periodic Table such as beryllium, magnesium, calcium, strontium and barium.

The process for producing the catalyst of the present invention comprising platinum/an alkali or alkaline earth metal compound/aluminum oxide (alumina) is not specifically limited, but may be in accordance with one of a variety of previously known processes.

Examples of the process for producing the catalyst of the present invention include the process in which alumina is impregnated simultaneously with a platinum compound and an alkali or alkaline earth metal compound to be supported thereon; the process in which aluminum oxide is impregnated once with a platinum compound followed by impregnating the aluminum oxide with an alkali or alkaline earth metal compound; and conversely the process in which the mixture of an alkali or alkaline earth metal compound with aluminum oxide is impregnated with a platinum compound.

In the case of impregnating aluminum oxide with a platinum compound, there are preferably employed as the platinum source a solution of chloroplatinic acid (IV) or tetraammineplatinum (II) complex in water or a suitable organic solvent such as methanol and acetone.

There are available a variety of methods and conditions for supporting a platinum compound on aluminum oxide, of which is preferable the method wherein the platinum compound is uniformly dispersed on aluminum oxide while being adjusted in the amount to be supported thereon. For the purpose of such uniform dispersion, the competitive adsorption method is favorable and exemplified by the method in which aluminum oxide is impregnated with chloroplatinic acid by adding an inorganic acid such as hydrochloric acid and nitric acid or an organic acid such as citric acid is added to the platinum-impregnated solution.

There is no specific limitation to the method for adding an alkali or alkaline earth metal compound to aluminum oxide in preparing the catalyst of the present invention insofar as the compound is uniformly dispersed on the aluminum oxide. There are available, for example, the method in which aluminum oxide is impregnated with a solution of a salt of such metal; the method in which aluminum oxide is kneaded with the above solution; the method in which the above solution is simultaneously added to the production process of aluminum oxide; and the like methods.

The ordinary process for preparing the catalyst of the present invention comprises, as described hereinbefore, impregnating aluminum oxide with a platinum component, followed by drying and calcining to obtain the platinum component-supported alumina and then adding the aforestated alkaline component. There is also adaptable the process wherein a platinum component and an alkaline component are supported on alumina at the same time.

The platinum-alkali-supporting alumina thus prepared is dried at a temperature not lower than room temperature, preferably in the range of 70° to 130° C. and then calcined at a temperature ranging from 300° to 800° C., followed by molding, if necessary, to be used for cyclization dehydrogenation reaction as the catalyst according to the present invention.

It is desirable that the catalyst of the present invention be treated, prior to actual use, with hydrogen at 300° to 700° C. to reduce the platinum compound into metallic platinum. The omission of the reduction operation will reduce the yield of the objective substance because of the generation of induction period during the reaction.

2-Methyl-1-(p-tolyl)butene to be subjected to cyclization dehydrogenation reaction in the present invention can contain the following six (6) isomers due to double bond position and geometry including cis and trans forms.

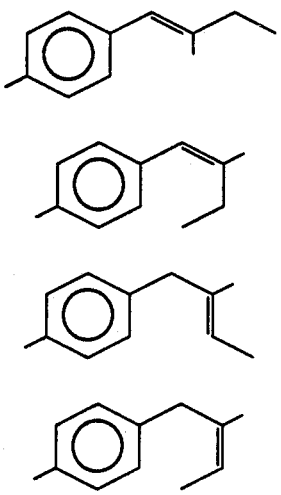

(1)

(2)

(3)

(4)

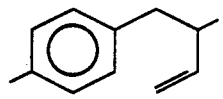

(5)

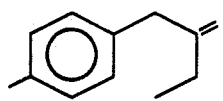

(6)

Any of the above-illustrated isomers alone or in the form of mixture with at least one other isomer may be put into application without any problem.

There is proposed a process for industrial production of 2-methyl-1-(p-tolyl)butene from the raw material for general purpose as follows:

For example, U.S. Pat. No. 5,008,479 discloses a process for producing 2-methyl-1-(p-tolyl)butene which comprises the steps of (1) acylation step in which toluene, butene and carbon monoxide are synthesized into 2,4-di-methylisobutyrophenone; (2) hydrogenation step in which the resultant 2,4-dimethyl-isobutyrophenone is hydrogenated into p-tolyl-sec butyl carbinol; and (3) dehydration step in which the resultant p-tolyl-sec-butyl carbinol is dehydrated into 2-methyl-1-(p-tolyl)-butene. In the above-mentioned process, the objective 2-methyl-1-(p-tolyl)butene obtained through the dehydration step comprises as pricipal ingredients the isomers [1] and [2] among the above-illustrated six isomers but can be made into a mixture comprising all types of the aforestated isomers by appropriately selecting the type of catalyst or reaction conditions in the above dehydration step.

According to the above-described process, the objective 2-methyl-1-(p-tolyl)butene can be produced in a high selectivity at a low cost from a widely available starting raw material. In addition to the above-described process, various processes may be employed.

Examples of the process for producing the publicly known 2-methyl-1-(p-tolyl)butane include the process wherein butene is addition-reacted with p-xylene in the presence of an alkali metal catalyst (refer to Japanese Patent Application Laid-Open Nos. 93952/1975 and 209027/1987), the process wherein 2,4-dimethylisobutyrophenone is subjected to hydrogenation dehydration as disclosed in the above U.S. Pat. No. 5,008,479 and various different processes.

In the production of 2,6-dimethylnaphthalene by the cyclization dehydrogenation reaction of 2-methyl-1-(p-tolyl)butene and/or 2-methyl-1-(p-tolyl)butane using the catalyst of the present invention, the reaction pressure may be lower than, equal to or higher than atmospheric pressure but is preferably in the range of atmospheric pressure to 2 kg/cm² with the reaction temperature of 350° to 700° C., preferably 450° to 650° C.

In the case where 2-methyl-1-(p-tolyl)butane is used as the starting material, it is necessary to raise the reaction temperature or decrease the SV (space velocity) in order to compensate for the reactivity of the above material some what lower than that of 2-methyl-1-(p-tolyl)butene in the cyclization dehydrogenation.

The objective 2,6-dimethylnaphthalene is in the form of solid having 112° C. melting point and preferably produced from 2-methyl-1-(p-tolyl)butene or 2-methyl-1-(p-tolyl)butane as the starting raw material by dissolving or diluting the material in or with toluene, benzene, steam or the like in view of the reaction procedure and also the purpose of suppressing side reactions such as polymerization.

The process according to the present invention enables the production of highly pure 2,6-dimethylnaphthalene in a high yield at a low cost by the use of the catalyst with high safety and stability from the widely available starting material, thereby rendering itself highly significant in the related industrial field.

In the following, the present invention will be specifically described with reference to examples and comparative examples, but shall not be limited thereto.

EXAMPLE 1

An aqueous solution of 2.65 g of chloroplatinic acid in diluted hydrochloric acid was incorporated with 100 g of alumina under stirring at 50° C. for 2 hours to carry out impregnation. The water in the mixture was distilled away at 70° C. under reduced pressure and then the residual mixture was dried overnight at 115° C. and calcined at 550° C. in the air to prepare a preparatory catalyst of platinum component supported on alumina. The preparatory catalyst was added to an aqueous solution of 29.8 g of lithium nitrate with stirring at 50° C. for 2 hours to effect further impregnation. The resultant mixture was dried at 70° C. under reduced pressure and then at 115° C. overnight, followed by calcining at 550° C. in the air.

Subsequently 10 g of the above platinum-lithium-alumina catalyst was packed in a tubular reactor made of quartz glass with 12 mm inside diameter and 300 mm length, reduced at 550° C. for 5 hours in a stream of hydrogen and maintained at 520° C. Then 2-methyl-1-(p-tolyl)butene mixture [48% 2-methyl-1-(p-tolyl)-1-butene, 41% 2-methyl-1-(p-tolyl)-2-butene and 11% other isomers] was dissolved in toluene to prepare 10% by weight of solution, which was vaporized at 10 g/hour through a preheating layer, and the resultant vapor was fed to the catalyst layer together with N$_2$ gas of 50 ml/min to carry out cyclization dehydrogenation reaction at atmospheric pressure.

The reaction product in the form of liquid was analyzed for conversion efficiency of 2-methyl-1-(p-tolyl)-butene mixture and selectivity to 2,6-dimethylnaphthalene. The results are given in Table 1.

EXAMPLE 2

An aqueous solution of 2.65 g of chloroplatinic acid in diluted hydrochloric acid was incorporated with 200 g of alumina under stirring at 50° C. for 2 hours to carry out impregnation. The water in the mixture was distilled away at 70° C. under reduced pressure and then the residual mixture was dried overnight at 115° C. and calcined at 550° C. in the air to prepare a preparatory catalyst of 0.5% by weight of platinum component supported on alumina. The preparatory catalyst in an amount of ¼ of the total was added to an aqueous solution of 29.8 g of lithium nitrate with stirring at 50° C. for 2 hours to effect further impregnation. The resultant mixture was dried at 70° C. under reduced pressure and then at 115° C. overnight, followed by calcining at 550° C. in the air.

Subsequently 10 g of the above platinum-lithium-alumina catalyst was packed in a tubular reactor made of quartz glass with 12 mm inside diameter and 300 mm length, reduced at 550° C. for 5 hours in a stream of hydrogen and maintained at 520° C. Then 2-methyl-1-(p-tolyl)butene mixture [62% 2-methyl-1-(p-tolyl)-1-butene, 26% 2-methyl-1-(p-tolyl)-2-butene and 12% other isomers] was dissolved in toluene to prepare 10% by weight of solution, which was vaporized at 10 g/hour through a preheating layer, and the resultant vapor was fed to the catalyst layer together with N$_2$ gas of 50 ml/min to carry out cyclization dehydrogenation reaction at atmospheric pressure.

The reaction results are given in Table 1.

Example 3

The procedure in Example 2 was repeated to carry out cyclization dehydrogenation reaction except that distilled water was fed to the catalyst layer at 1 g/hour via the preheating layer in addition to 2-methyl-1-(p-tolyl)butene mixture at 10 g/hour. The reaction results are given in Table 1.

EXAMPLE 4

The procedure in Example 2 was repeated to carry out cyclization dehydrogenation reaction except that 3.88 g of potassium nitrate was used in place of lithium nitrate to prepare a catalyst of 0.5% platinum/3% potassium supported on alumina. The reaction results are given in Table 1.

EXAMPLE 5

The procedure in Example 4 was repeated to carry out cyclization dehydration reaction except that distilled water was fed to the catalyst layer at 1 g/hour via the preheating layer in addition to 2-methyl-1-(p-tolyl)-butene mixture at 10 g/hour. The reaction results are given in Table 1.

COMPARATIVE EXAMPLE 1

The procedure in Example 2 was repeated to carry out cyclization dehydration reaction except that the catalyst of 0.5% by weight of platinum component supported on alumina obtained in Example 2 was used as such without the impregnation of the alkali metal. The reaction results are given in Table 1.

COMPARATIVE EXAMPLE 2

Alumina in an amount of 100 g was added to an aqueous solution of 29.8g of lithium nitrate under stirring at 50° C. for 2 hours to effect impregnation. The resultant mixture was dried at 70° C. under reduced pressure and then at 115° C. overnight, followed by calcining at 550° C. in the air.

Subsequently 10 g of the above lithium-alumina catalyst was packed in a tubular reactor made of quartz glass with 12 mm inside diameter and 300 mm length and maintained at 520° C. Then, a solution of 10% by weight of 2-methyl-1-(p-tolyl)butene mixture in toluene same as that in Example 2 was vaporized at 10 g/hour through a preheating layer, and the resultant vapor was fed to the catalyst layer together with N$_2$ gas of 50 ml/min to carry out cyclization dehydrogenation reaction at atmospheric pressure. The reaction results are given in Table 1.

COMPARATIVE EXAMPLE 3

The procedure in Comparative Example 2 was repeated to carry out cyclization dehydrogenation reaction except that 7.76 g of potassium nitrate was used in place of lithium nitrate to prepare a catalyst of 3% by weight of potassium component supported on alumina. The reaction results are given in Table 1.

EXAMPLES 6 to 12

The catalysts were prepared in the same manner as in Example 2 so as to obtain alkali metal compounds each in a prescribed amount supported on alumina as in Table 1, reduced similarly to Example 2 and used for cyclization dehydrogenation reaction to examine the activity of each of the catalysts. The results are given in Table 1.

EXAMPLE 13

The procedure in Example 1 was repeated to carry out cyclization dehydration reaction except that 796 g of chloroplatinic acid and 7.75 g of potassium nitrate were used in place of lithium nitrate. The results are given in Table 1.

EXAMPLE 14

An aqueous solution of 0.31 g of tetraammineplatinum (II) nitrate [$(NH_3)_4Pt(NO_3)_2$] and 2.41 g of potassium nitrate was incorporated with 30 g of alumina under stirring at 50° C. for 2 hours to carry out impregnation. The water in the mixture was distilled away at 70° C. under reduced pressure and then the residual mixture was dried overnight at 115° C. and calcined at 550° C. in the air to prepare a catalyst of platinum-potassium supported on alumina.

Subsequently 10 g of the above platinum-potassium-alumina catalyst was packed in a tubular reactor made of quartz glass with 12 mm inside diameter and 300 mm length, reduced at 550° C. for 5 hours in a stream of hydrogen and maintained at 520° C. Then 2-methyl-1-(p-tolyl)butene mixture [35% 3-methyl-4-(p-tolyl)-1-butene, 62% 2-methyl-1-(p-tolyl)-2-butene and 3% other isomers] was dissolved in toluene to prepare 10% by weight of solution, which was vaporized at 10 g/hour through a preheating layer, and the resultant vapor was fed to the catalyst layer together with $N_2$ gas of 50 ml/min to carry out cyclization dehydrogenation reaction at atmospheric pressure.

The reaction results are given in Table 1.

EXAMPLE 15

An aqueous solution of 1.94 g of potassium nitrate was incorporated with 0.5% by weight of platinum-alumina catalyst produced by N. E. Chemcat Corporation in an amount of 25 g under stirring at 50° C. for 2 hours to carry out impregnation. The water in the mixture was distilled away at 70° C. under reduced pressure.

Subsequently 10 g of the above platinum-potassium nitrate-alumina catalyst was packed in a tubular reactor made of quartz glass with 12 mm inside diameter and 300 mm length, reduced at 550° C. for 5 hours in a stream of hydrogen to decompose the nitrate and maintained at 520° C. Then 2-methyl-1-(p-tolyl)butene mixture [48% 2-ethyl-3-(p-tolyl)-2-propene, 41% 2-methyl-1-(p-tolyl)-2-butene and 11% other isomers] was dissolved in toluene to prepare 10% by weight of solution, which was vaporized at 10 g/hour through a preheating layer, and the resultant vapor was fed to the catalyst layer together with $N_2$ gas of 50 ml/min to carry out cyclization dehydrogenation reaction at atmospheric pressure.

The reaction results are given in Table 1.

EXAMPLE 16

An aqueous solution of 0.66 g of chloroplatinic acid was incorporated with 50 g of oxide complex consisting of calcium oxide and aluminum oxide (atomic ratio of 1:4) under stirring at 50° C. for 2 hours to carry out impregnation. The water in the mixture was distilled away at 70° C. under reduced pressure.

Subsequently 10 g of the above platinum-potassium-alumina catalyst was packed in a tubular reactor made of quartz glass with 12 mm inside diameter and 300 mm length, reduced at 550° C. for 5 hours in a stream of hydrogen and maintained at 520° C. Then 2-methyl-1-(p-tolyl)butene mixture [62% 2-methyl-1-(p-tolyl)-1-butene, 26% 2-methyl-1-(p-tolyl)-2-butene and 12% other isomers] was dissolved in toluene to prepare 10% by weight of solution, which was vaporized at 10 g/hour through a preheating layer, and the resultant vapor was fed to the catalyst layer together with $N_2$ gas of 50 ml/min to carry out cyclization dehydrogenation reaction at atmospheric pressure.

The reaction results are given in Table 1.

EXAMPLE 17

The catalyst as used in Example 16 was reduced similarly to Example 16 and the reaction temperature was maintained at 530° C. Separately, 2-methyl-1-(p-tolyl)-butane was dissolved in benzene to prepare a solution containing the same by 5% by weight, which was vaporized at 10 g/hour through a preheating layer, and the resultant vapor was fed to the catalyst layer together with $N_2$ gas of 50 ml/min to carry out cyclization dehydrogenation reaction at ordinary pressure.

As a result, the objective 2,6-dimethylnaphthalene (2,6-DMN) was obtained at a conversion efficiency of 2-methyl-1-(p-tolyl)butane of 82.9% and a selectivity to 2,6-DMN of 65.2%.

TABLE 1

| No. | Catalyst (*) | Platinum source | Alkali source | Temperature (°C.) | Water | Conversion efficiency (%) | Selectivity to 2,6-DMN** (%) |
|---|---|---|---|---|---|---|---|
| Example 1 | Pt(1)—Li(3) | $H_2PtCl_6$ | $LiNO_3$ | 520 | absent | 94.4 | 72.7 |
| Example 2 | Pt(0.5)—Li(3) | $H_2PtCl_6$ | $LiNO_3$ | 520 | absent | 96.9 | 71.2 |
| Example 3 | Pt(0.5)—Li(3) | $H_2PtCl_6$ | $LiNO_3$ | 530 | present | 93.4 | 72.9 |
| Example 4 | Pt(0.5)—K(3) | $H_2PtCl_6$ | $KNO_3$ | 520 | absent | 95.8 | 73.3 |
| Example 5 | Pt(0.5)—K(3) | $H_2PtCl_6$ | $KNO_3$ | 530 | present | 95.6 | 74.9 |
| Comparative Example 1 | Pt(0.5) | $H_2PtCl_6$ | — | 480 | absent | 98.0 | 22.8 |
| Comparative Example 2 | Li(2) | — | $LiNO_3$ | 520 | absent | 33.3 | 26.8 |
| Comparative Example 3 | K(3) | — | $KNO_3$ | 520 | absent | 77.0 | 61.3 |
| Example 6 | Pt(0.5)—Na(3) | $H_2PtCl_6$ | $NaNO_3$ | 520 | present | 94.7 | 73.4 |
| Example 7 | Pt(0.5)—Na(3) | $H_2PtCl_6$ | $Na_2CO_3$ | 520 | present | 94.4 | 73.4 |
| Example 8 | Pt(0.5)—K(2) | $H_2PtCl_6$ | $KNO_3$ | 530 | absent | 97.0 | 71.4 |
| Example 9 | Pt(0.5)—K(5) | $H_2PtCl_6$ | $KNO_3$ | 520 | absent | 93.5 | 69.7 |
| Example 10 | Pt(0.5)—K(3) | $H_2PtCl_6$ | $K_2SO_4$ | 530 | present | 96.2 | 74.3 |

TABLE 1-continued

| No. | Catalyst (*) | Platinum source | Alkali source | Temperature (°C.) | Water | Conversion efficiency (%) | Selectivity to 2,6-DMN** (%) |
|---|---|---|---|---|---|---|---|
| Example 11 | Pt(0.5)—K(3) | H$_2$PtCl$_6$ | KOH | 520 | absent | 93.9 | 74.6 |
| Example 12 | Pt(0.5)—Cs(3) | H$_2$PtCl$_6$ | CsNO$_3$ | 530 | absent | 95.9 | 74.3 |
| Example 13 | Pt(3)—K(3) | H$_2$PtCl$_6$ | KNO$_3$ | 520 | present | 97.4 | 73.7 |
| Example 14 | Pt(0.5)—K(3) | (NH$_3$)$_4$Pt(NO$_3$)$_2$ | KNO$_3$ | 520 | absent | 95.0 | 70.4 |
| Example 15 | Pt(0.5)—K(3) | — | KNO$_3$ | 520 | absent | 97.4 | 68.8 |
| Example 16 | Pt(0.5) | H$_2$PtCl$_6$ | CaO | 530 | absent | 97.4 | 72.7 |

*Figure in parenthesis shows % by weight based on alumina weight.
**2,6-dimethylnaphthalene

What is claimed is:

1. A process for production of 2,6-dimethylnaphthalene which comprises contacting at least one starting material selected from the group consisting of 2-methyl-1-(p-tolyl) butene and 2-methyl-1-(p-tolyl)butane with a catalyst comprising a platinum component and at least one component selected from the group consisting of alkali metals and alkaline earth metals each being supported on aluminum oxide to form 2,6-dimethylnaphthalene by simultaneous cyclization dehydrogenation; the amount of said platinum is 0.05 to 20% by weight and the amount of said alkali metal or alkaline earth metal is 1 to 10% by weight each based on aluminum oxide.

2. The process according to claim 1 wherein said catalyst comprises a platinum component and at least one component selected from alkali metals each being supported on aluminum oxide.

3. The process according to claim 1 wherein said catalyst comprises a platinum component and at least one component selected from alkaline earth metals, each being supported on aluminum oxide.

4. The according to claim 2 wherein said alkali metals are selected from the group consisting of sodium potassium, lithium and cesium.

5. The process according to claim 3 wherein said alkaline earth meals are selected from the group consisting of beryllium, magnesium, calcium and strontium.

6. The process according to claim 1 wherein said contacting is effected at a temperature in the range of 300° to 700° C. and a pressure in the range of atmospheric pressure to 2 kg/cm$^2$G.

7. The process according to claim 1 wherein said starting raw material is at least one 2-methyl-1(p-tolyl)-butene isomer selected from the group consisting of 2-methyl-1-(p-tolyl)-1-butene, 2-methyl-1(p-tolyl)-2-butene, 3-methyl-4-(p-tolyl)-1-butene and 2-ethyl-3-(p-tolyl)-2-propene.

8. The process according to claim 1 wherein the amount of said platinum is 0.1 to 10% by weight based on aluminum oxide.

9. The process according to claim 2 wherein
said contacting is effected at a temperature in the range of 330° to 700° C. and a pressure in the range of atmospheric pressure to 2 kg/cm$^2$G;
said starting raw material is at least one 2-methyl-1(p-tolyl)butene isomer selected from the group consisting of 2-methyl-1-(p-tolyl)-1-butene, 2-methyl-1-(p-tolyl)-2-butene, 3-methyl-4-(p-tolyl)-1-butene and, 2-ethyl-3-(p-tolyl)-2-propene; and
wherein the amount of said platinum is 0.1 to 10% by weight based on aluminum oxide.

10. The process according to claim 9, wherein said alkali metals are selected from the group consisting of sodium, potassium, lithium and cesium.

11. The process according to claim 3, wherein
said contacting is effected at a temperature in the range of 300° to 700° C. and a pressure in the range of atmospheric pressure to 2 kg/cm$^2$G;
said starting raw material is at least one 2-methyl-1-(p-tolyl)butene isomer selected from the group consisting of 2-methyl-1-(p-tolyl)-1-butene, 2-methyl-1-(p-tolyl)-2-butene, 3-methyl-4-(p-tolyl)-1-butene and 2-ethyl-3-(p-tolyl)-2-propene; and
wherein the amount of said platinum is 0.1 to 10% by weight based on aluminum oxide.

12. The process according to claim 11, wherein said alkaline earth metals are selected from the group consisting of beryllium, magnesium, calcium and strontium.

* * * * *